(12) United States Patent
Abbott

(10) Patent No.: US 6,214,314 B1
(45) Date of Patent: Apr. 10, 2001

(54) PROCESS FOR THE PREPARATION METHANOL AND HYDROGEN

(75) Inventor: Peter Edward James Abbott, Cleveland (GB)

(73) Assignee: Imperial Chemical Industries PLC (GB)

( * ) Notice: Subject to any disclaimer, the term of this patent is extended or adjusted under 35 U.S.C. 154(b) by 0 days.

(21) Appl. No.: 09/482,720

(22) Filed: Jan. 13, 2000

Related U.S. Application Data

(63) Continuation of application No. PCT/GB98/01859, filed on Jun. 24, 1998.

(30) Foreign Application Priority Data

Jul. 15, 1997 (GB) .................................................. 9714744

(51) Int. Cl.$^7$ ................ C01B 3/24; C01B 3/26
(52) U.S. Cl. ............ 423/650; 423/651; 423/652; 518/704
(58) Field of Search ................... 423/650, 651, 423/652; 518/704

(56) References Cited

U.S. PATENT DOCUMENTS 4,367,206 * 1/1983 Pinto .................................. 423/359

FOREIGN PATENT DOCUMENTS 0 624 388   11/1994   (EP) .

* cited by examiner

*Primary Examiner*—Wayne Langel
(74) *Attorney, Agent, or Firm*—Pillsbury Winthrop LLP

(57) ABSTRACT

Process for the co-production of hydrogen and methanol by steam reforming a hydrocarbon feedstock, condensing and separating steam from the reformed gas, synthesizing methanol from the resultant de-watered reformed gas without further compression, separating synthesized methanol and separating hydrogen from the residual gas, optionally after subjecting the residual gas to the shift reaction is disclosed.

6 Claims, 1 Drawing Sheet

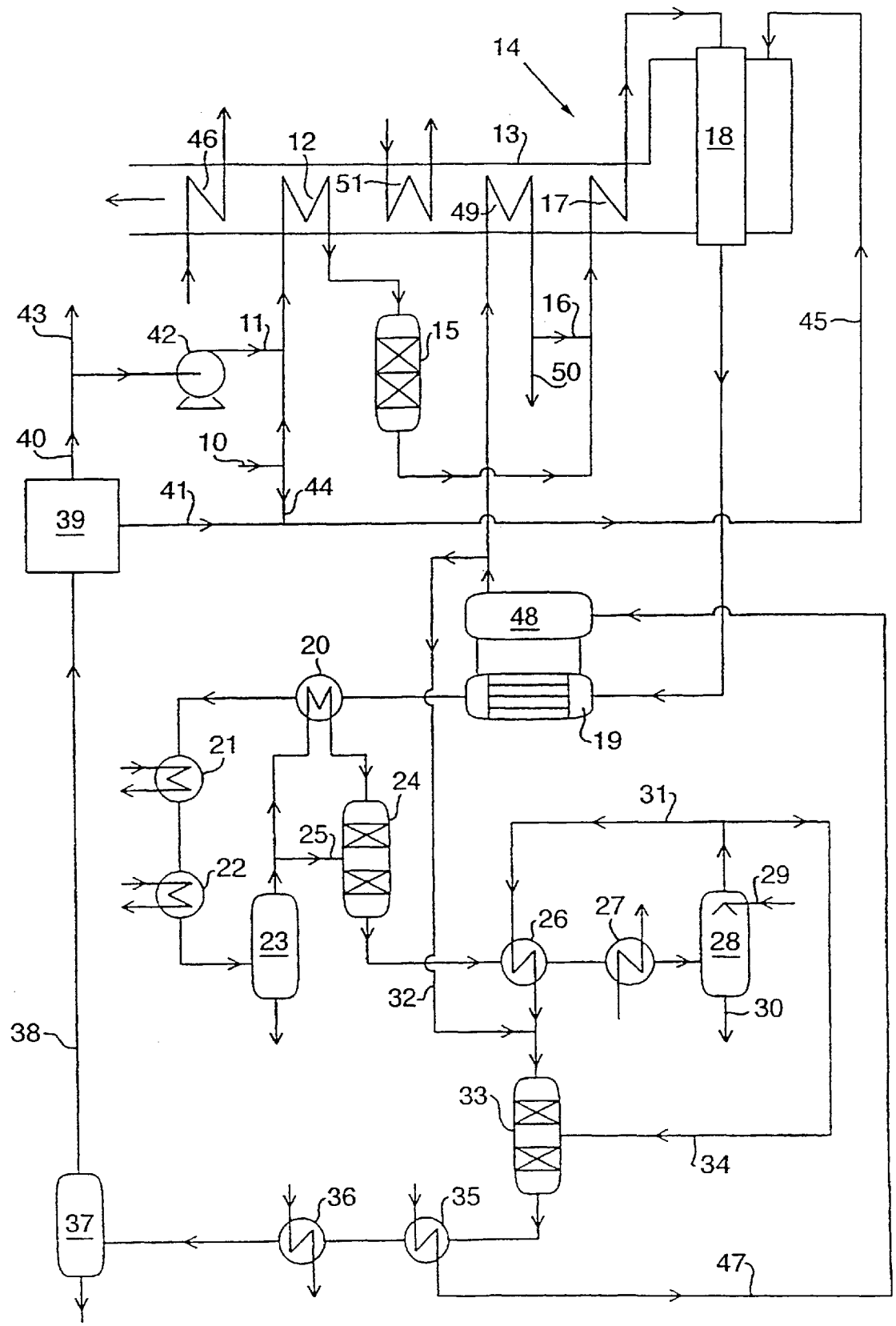

PROCESS FOR THE PREPARATION METHANOL AND HYDROGEN

This application is a continuation of PCT/GB98/01857, filed Jun. 24, 1998.

This invention relates to the production of methanol. There is an increasing demand for methanol for the production of motor fuel additives such as methyl t-butyl ether (MTBE) and t-amyl methyl ether (TAME). These additives are produced as a result of the reaction of methanol with the appropriate olefin, e.g. isobutene in the case of MTBE. The relevant olefins are normally produced by cracking a suitable hydrocarbon feedstock e.g. at a refinery. Conveniently the additives are manufactured at, or adjacent to, the source, e.g. refinery, of the relevant olefins. A typical refinery may produce 2500 US barrels/day (approx. 400 m$^3$/d) of MTBE for which about 110 te/day of methanol is required. Typical refinery methanol requirements are in the range 50–200 te/d. Usually the methanol is imported to the site from a methanol plant which typically produces 1500–3000 te/d.

Many processes operating at refineries require hydrogen as a reactant: while hydrogen is generally produced as a byproduct of naphtha catalytic reforming, there is often a need for further hydrogen supplies than are produced by such reforming. As a consequence many refineries also incorporate a hydrogen plant. Typical refinery hydrogen plants have a capacity in the range 50–200 te/d of hydrogen. We have realised that there are economic advantages in arranging for that hydrogen plant to be integrated with a methanol plant of sufficient size to provide the methanol required at the refinery for production of MTBE and/or TAME.

We have devised such an integrated process. Hydrogen is normally manufactured by steam reforming a hydrocarbon feedstock, such as methane, natural gas, or naphtha, at an elevated temperature and pressure producing a reformed gas stream containing hydrogen, carbon oxides, steam and methane, followed by subjecting the reformed gas stream to the shift reaction to convert carbon monoxide in the reformed gas to carbon dioxide with the production of an equivalent amount of hydrogen, and then separating the hydrogen from the shifted gas stream. The separation is often effected by an adsorption process, such as pressure swing adsorption, after condensing out the steam from the shifted gas. The waste gas, containing methane, carbon oxides and a small proportion of hydrogen, from the separation step is generally used as fuel in the steam reforming process. We have realised that if the steam is condensed from the reformed gas and then the de-watered reformed gas is subjected to a step of methanol synthesis, without any further compression, a significant amount of methanol can be produced. This methanol can be separated and then hydrogen can be separated from the residual gas, optionally after subjecting the residual gas to the shift reaction after adding steam. By this route it is possible to produce sufficient methanol to meet the refinery requirements for only a moderate increase in the size of the refinery hydrogen plant. The present invention may be used to modify an existing hydrogen plant to provide for co-production of hydrogen and methanol.

Accordingly the present invention provides a process for the co-production of hydrogen and methanol comprising a) subjecting a hydrocarbon feedstock to steam reforming at an elevated pressure and temperature to produce a reformed gas stream containing hydrogen, carbon oxides, methane and unreacted steam;

b) cooling the reformed gas to condense steam therein and separating condensed water;

c) without further compressing the resultant de-watered reformed gas, subjecting the de-watered reformed gas to methanol synthesis and separating synthesised methanol from the product to leave an unreacted gas stream; and d) separating hydrogen from the unreacted gas stream, optionally after adding steam to said unreacted gas and subjecting the mixture of unreacted gas and steam to the shift reaction.

Prior to steam reforming, the hydrocarbon feedstock, e.g. methane, natural gas, associated gas, or naphtha, should be desulphurised, for example by addition of a small proportion of hydrogen and passage of the mixture over a hydrodesulphurisation catalyst such as nickel or cobalt molybdate followed by absorption of hydrogen sulphide produced by the hydrodesulphurisation reaction with a suitable absorbent, especially a bed of a particulate zinc oxide or zinc carbonate composition.

The steam reforming reaction is an endothermic reaction and is normally effected by passing a mixture of the desulphurised hydrocarbon feedstock and steam through tubes containing a steam reforming catalyst, normally nickel supported on a shaped support such as rings of alumina or a calcium aluminate cement, while strongly heating the tubes. The tubes are usually heated in a furnace fuelled with a suitable hydrocarbon-containing stream; alternatively the tubes may be located within a high temperature convective heat exchange reformer, for example as described in GB 1 578 270. In this type of heat exchange reformer, the catalyst is disposed in tubes extending between a pair of tube sheets through a heat exchange zone. Reactants are fed to a zone above the upper tube sheet and pass through the tubes and into a zone beneath the lower tube sheet. The heating medium, for example the hot product of combusting a fuel with air, is passed through the zone between the two tube sheets.

As described hereinafter, whichever type of reformer is employed, the fuel used to provide the heat to heat the reformer tubes may in at least part be the waste gas remaining after separation of the desired hydrogen product. The tubes are generally heated to such an extent that the reformed gas leaves the catalyst at a temperature in the range 750–950° C., especially 800–900° C. The steam reforming reaction is operated at an elevated pressure. The pressure is generally in the range 20–50 bar abs., and preferably is in the range 25–40 bar abs.

The steam may be introduced by direct injection of steam and/or by saturation of the feedstock by contact of the latter with a stream of heated water. The amount of steam introduced is preferably such as to give a steam ratio in the range 2 to 3.5 moles of steam per gram atom of hydrocarbon carbon in the feedstock.

Before the endothermic reforming step, the hydrocarbon steam mixture may be subjected to a step of adiabatic low temperature reforming. In such a process, the hydrocarbon steam mixture is heated, typically to a temperature in the range 400–600° C., and then passed adiabatically through a bed of a suitable catalyst, usually a catalyst having a high nickel content, for example above 40% by weight. During such an adiabatic low temperature reforming step any hydrocarbons higher than methane react with steam to give a mixture of methane, carbon oxides and hydrogen. The use of such an adiabatic reforming step, commonly termed pre-reforming, is desirable to ensure that the feed to the endothermic reforming step contains no hydrocarbons higher than methane and also contains a significant amount of hydrogen. This is desirable in order to minimise the risk of carbon formation on the catalyst in the reformer tubes.

After any such pre-reforming step the feedstock/steam mixture is further heated, if necessary, to the reformer tubes inlet temperature which is typically in the range 450–600° C.

The reformed gas from the endothermic reforming step is then subjected to heat recovery, usually by steam raising to provide the process steam. Also by heat exchange, heat may be recovered from the reformed gas and/or from the gases used to heat the reformer tubes, to provide heat for heating the feedstock/steam mixture to the reformer inlet temperature and/or, where a step of pre-reforming is used, to heat the feedstock/steam mixture to the pre-reformer inlet temperature and/or to heat the pre-reformed gas to the desired inlet temperature of the reformer tubes.

After heat recovery as aforesaid from the reformed gas, the reformed gas is cooled to condense the excess of steam therein as water. The condensed water is then separated to give a de-watered reformed gas. If desired, the cooling can be effected by direct injection of water: this gives a stream of heated water which then may be further heated, e.g. by heat exchange with the hot reformed gas, to give a stream of hot water to be used for saturation to introduce the process steam.

The de-watered reformed gas is then subjected to methanol synthesis: the de-watered reformed gas, without any further compression, is heated to the desired synthesis inlet temperature, which is typically in the range 20–300° C., especially 220–250° C., and contacted with a methanol synthesis catalyst. The latter is preferably shaped particles, e.g. pellets, of a copper catalyst obtained by reduction of a precursor consisting of copper oxide and one or more supporting components such as chromia, magnesia, zinc oxide or alumina. Preferred precursors are those obtained by calcination of a co-precipitated mixture of copper, zinc, aluminium, and optionally also magnesium compounds. The methanol synthesis reaction is exothermic and the equilibrium is favoured towards methanol synthesis by low temperatures. However the catalytic activity increases as the temperature is increased. It is preferred to effect the synthesis reaction with a reactor outlet temperature in the range 20–260° C., preferably below 250° C.

The methanol synthesis may be effected in a synthesis reactor of the "quasi isothermal" type wherein the catalyst temperature is maintained essentially constant by heat exchange means in the reactor whereby heat evolved by the synthesis reaction is transferred to a coolant, which is preferably boiling water. The coolant may circulate through tubes extending through the catalyst bed. An example of this type of reactor is described in EP 81 948. Alternatively, but less preferably, the catalyst may be disposed in tubes and the coolant circulated around the exterior of the tubes. Alternatively, a reactor of the type disclosed in U.S. Pat. No. 4,778,662 where the catalyst bed is cooled by heat exchange with the incoming synthesis gas may be employed but in this case it is preferred, unlike the reactor described in that reference, that there is little or no adiabatic bed below the cooling tubes. An alternative type of reactor, is a reactor of the so-called "quench" type. In this type of reactor the catalyst is disposed as multiple beds and part of the synthesis gas is fed to the first bed and part is injected as "quench" gas into the reactor between beds to moderate the reaction. Alternatively a single bed "quench" reactor may be employed wherein the catalyst is disposed as a single bed and part of the synthesis gas is fed to the bed inlet and part is injected as "quench" gas part way through the bed. In either single bed or multiple bed quench reactors there may be multiple injections of the quench gas.

After synthesis, the reacted gas is cooled, for example by feed/effluent heat exchange, i.e. by heat exchange with the de-watered reformed gas to heat the latter to the desired synthesis inlet temperature, and then by heat exchange with a suitable coolant to condense methanol as a liquid. The condensed methanol is then separated leaving a stream of unreacted gas. In some cases it may be desirable to scrub the unreacted gas with cold water. Thus trays or a packed section may be disposed in the separator and cold water injected into the upper part of the separator. Since the methanol synthesis pressure employed is relatively low, the equilibrium vapour phase above the liquid phase crude methanol contains a significant amount of the methanol produced. The water scrubbing can be used to recover a substantial portion of the methanol from this vapour phase.

In some cases, it may be desirable to employ a series of two or more methanol synthesis stages with separation of synthesised methanol after each stage. Whether such multiple methanol stages are employed will depend on a number of factors including the relative demand for methanol and hydrogen from the plant. Thus, by having multiple methanol synthesis stages, a higher yield of methanol can be obtained but less hydrogen will be available for recovery as the co-product.

The methanol synthesis step is operated without a step of compression in order to save compression costs: preferably the synthesis is operated as a "once-through" system although in some cases it may be desirable to employ a synthesis loop where some or all of the unreacted gas from the methanol separator is recycled and added to the dewatered reformed gas: part of the unreacted gas, or the mixture thereof with the dewatered reformed gas, is taken as a purge from the synthesis loop to prevent a build up of inerts and to provide the feed for the recovery of the desired product hydrogen.

After separation of the methanol, hydrogen is recovered from the residual gas. The residual gas will generally contain significant quantities of carbon monoxide and so it is often advantageous to convert at least some of that residual carbon monoxide to carbon dioxide. This may be done by adding steam to the residual gas and subjecting the mixture to the shift reaction. In the shift reaction carbon monoxide reacts with steam producing carbon dioxide and an equivalent amount of hydrogen.

The steam required for the shift reaction may be introduced by direct injection or by saturation by contact with a stream of hot water. The amount of steam introduced should be at least 4 times the amount of carbon monoxide in the residual gas. Depending on the carbon monoxide content of the residual gas and the desired carbon monoxide content of the product of the shift reaction, the shift reaction may be of the high temperature type, or low temperature type, or high temperature shift followed by low temperature shift.

In the high temperature shift process, the mixture of residual gas and steam is heated to a suitable inlet temperature, for example in the range 300 to 420° C., and passed over a high temperature shift catalyst, typically an iron oxide/chromia composition, often containing a small amount of copper.

In a low temperature shift process, the mixture of residual gas and steam, or the product from the high temperature shift process is passed, at an inlet temperature typically in the range 180 to 300° C. over a low temperature shift catalyst, typically a copper/zinc oxide/alumina composition. Where the feed to the low temperature shift stage is the product from a high temperature shift stage, cooling of the product from the high temperature shift stage to the desired low temperature shift inlet temperature is necessary.

In an alternative process, even where the carbon monoxide content of the residual gas is relatively high, the shift stage may be a single stage of low temperature shift effected in heat exchange with a coolant, for example as described in U.S. Pat. No. 4,721,611.

In yet another alternative, the shift reaction may be effected in a single stage with injection of quench gas to moderate the shift reaction in a manner similar to methanol synthesis using a quench reactor as aforesaid. In this instance, the quench gas may be part of the residual gas remaining after separation of methanol and to which no steam has been added. As in the case of methanol synthesis using a quench reactor, there may be multiple injections of the quench gas.

If one or more stages of shift reaction are employed, the extent of the shift reaction is preferably such that the shifted gas has a carbon monoxide content below 1% by volume on a dry basis.

After the shift reaction the shifted gas should be cooled to condense residual steam as water which is then separated to give a de-watered shifted gas.

If there is no shift reaction, no step of cooling and water removal from the residual gas is necessary after separation of the methanol.

Hydrogen is then recovered from the de-watered shifted gas, or from the residual gas if there is no shift reaction. This is conveniently effected by an adsorption process, for example a pressure swing adsorption process as is well known in the art. Such a process gives a product stream of hydrogen, typically of purity over 95%, and often over 99%, and a waste gas stream containing carbon oxides, methane and a small proportion of hydrogen. This waste gas may be used as fuel for the endothermic reforming step.

The methanol separated after the methanol synthesis stage or stages is normally purified by distillation. Heat required for such distillation may be provided by heat recovery from a suitable source, for example the hot reformed gas after initial heat recovery by steam raising. If the process of the invention is operated at a refinery to produce the methanol to be used for production of MTBE and/or TAME, the methanol does not need to be as pure as if the methanol is to be a traded product. As a consequence the distillation requirements need not be so rigorous and smaller and/or fewer columns can be employed.

One embodiment of the invention is illustrated by reference to the accompanying drawing which is a diagrammatic flowsheet of the process. In this embodiment the temperatures and pressures are for the purposes of illustration only.

A hydrocarbon feedstock, e.g. natural gas or naphtha, is supplied via line 10 at a pressure of 31 bar abs. Recycle hydrogen is added via line 11, and the mixture heated to 370° C. in a heat exchanger 12 in the convection section 13 of a reformer 14. The preheated mixture is then passed over a bed of a hydro-desulphurisation catalyst and a bed of an absorbent for hydrogen sulphide in a vessel 15. Steam at 40 bar abs. is added to the resultant desulphurised gas via line 16 and the mixture of steam and desulphurised feedstock is heated to 540° C. in heat exchanger 17 in the convection section 13 of the reformer and then fed at 30 bar abs. to the reformer tubes 18 containing a steam reforming catalyst. The reformed gas leaves the reformer tubes at a pressure of 26.8 bar abs. and at a temperature of 865° C.

Heat is recovered from the reformed gas in a boiler 19 and then in heat exchangers 20 and 21 and then the reformed gas is cooled to 40° C. in cooler 22. Condensed steam is separated from the cooled reformed gas in separator 23. The de-watered reformed gas is taken overhead from the separator 23 and part (about 34% of the total) is heated to 220° C., the desired methanol synthesis inlet temperature, in heat exchanger 20 and then fed to a methanol synthesis reactor 24. This contains five beds of methanol synthesis catalyst and the remaining 66% of the cool de-watered reformed gas bypasses heat exchanger 20 and is fed, via line 25, to reactor 24 as quench gas between the catalyst beds. The proportion of quench gas injected between each bed is such that the temperature of the gas fed to the next bed is in the range 206–214° C. The reacted gas leaves the methanol synthesis reactor 24 at 242° C. and at a pressure of 24 bar abs. and is cooled with heat recovery in heat exchanger 26 and then cooled to 40° C. in cooler 27. The cooled reacted gas is then passed to a wash column 28 where the condensed methanol is separated and methanol in the vapour phase is washed from the gas by a stream 29 of cold water. The resultant crude aqueous methanol stream is separated as stream 30.

Part (about 65%) of the residual unreacted gas taken overhead from wash column 28 via line 31 is heated in heat exchanger 26. Steam is added to the heated unreacted gas via line 32 and the mixture fed at 187° C. to a shift convener 33 containing four beds of a copper/zinc oxide/alumina low temperature shift catalyst. The remaining 35% of the cool unreacted gas taken overhead from wash column 28 bypasses heat exchanger 26 and is fed, via line 34, to shift converter 33 as quench gas between the catalyst beds. The proportion of quench gas injected between each bed is such that the temperature of the gas fed to the next bed is in the range 229–236° C.

The shifted gas leaves the converter 33 at 240° C. and 23 bar abs. and is cooled to 160° C. in heat exchanger 35 and then to 40° C. in cooler 36. The condensed steam is separated from the shifted gas in separator 37. The de-watered shifted gas is taken overhead from separator 37 and fed, via line 38, to a pressure swing adsorption unit 39. In pressure swing adsorption unit, the shifted gas is separated into a hydrogen stream 40 and a waste gas stream 41. Part of the hydrogen stream is fed, via line 42, to a compressor 43 to provide the hydrogen recycle stream 11, while the remainder forms the product hydrogen stream 43.

The waste gas stream 41, supplemented by part of the feed stock fed via line 44, is fed via line 45 to the reformer as the reformer fuel employed to heat the reformer tubes 18. The air required for the combustion in the reformer is preheated in a heat exchanger 46 in the convection section of the reformer 14.

Boiler feed water, which may include condensate separated in separators 23 and 37, is heated by heat exchange with the shifted gas in heat exchanger 35 and fed, via line 47, to a steam drum 48 where it provides the feed for the boiler 19. Part of the steam from steam drum 48 is used as the steam added, via line 32, to the heated unreacted gas. The remainder of the steam from drum 48 is superheated in heat exchanger 49 in the convection section of reformer 14. Part of the superheated steam is used as the process steam added, via line 16, to the desulphurised feedstock while the remainder is available for export via line 50. If necessary, further steam can be raised in heat exchanger 51 in the convection section of the reformer.

The heat recovered in heat exchanger 21 can be used to provide the heat necessary for distillation of the crude methanol.

The invention is further illustrated by the following calculated examples.

EXAMPLE 1

In this example the procedure of the above described flowsheet is employed using natural gas as the feedstock to produce about 90 te/day of crude methanol and about 80 te/day of hydrogen. The temperature, pressure, and flow rates (rounded to the nearest integer) of the various streams are shown in the following table.

TABLE 1

| Stream | T (° C.) | P (bar abs.) | CH$_4$ | H$_2$ | CO | CO$_2$ | N$_2$ | H$_2$O | CH$_3$OH |
|---|---|---|---|---|---|---|---|---|---|
| total natural gas feed | 40 | 31 | 897* | 0 | 0 | 5 | 7 | 0 | 0 |
| natural gas fuel | 40 | 31 | 197* | 0 | 0 | 1 | 1 | 0 | 0 |
| natural gas process feed | 40 | 31 | 700* | 0 | 0 | 4 | 5 | 0 | 0 |
| hydrogen recycle | 40 | 31 | 0 | 39 | 0 | 0 | 0 | 0 | 0 |
| process steam | 340 | 40 | 0 | 0 | 0 | 0 | 0 | 2099 | 0 |
| reformer feed | 540 | 30 | 700* | 39 | 0 | 4 | 5 | 2099 | 0 |
| reformed gas | 865 | 27 | 131 | 1897 | 365 | 208 | 5 | 1327 | 0 |
| de-watered reformed gas | 40 | 27 | 131 | 1897 | 365 | 207 | 5 | 8 | 0 |
| ex-methanol synthesis | 242 | 24 | 131 | 1652 | 253 | 201 | 5 | 15 | 119 |
| wash water | 40 | 40 | 0 | 0 | 0 | 0 | 0 | 50 | 0 |
| crude methanol | 40 | 24 | 0 | 0 | 0 | 1 | 0 | 63 | 117 |
| unreacted gas to shift | 40 | 24 | 131 | 1652 | 253 | 200 | 5 | 2 | 2 |
| shift steam | 252 | 40 | 0 | 0 | 0 | 0 | 0 | 1000 | 0 |
| shift inlet | 188 | 24 | 85 | 1074 | 164 | 130 | 3 | 1001 | 1 |
| total shift quench | 40 | 24 | 46 | 578 | 88 | 70 | 2 | 1 | 1 |
| shifted gas | 240 | 23 | 131 | 1892 | 12 | 440 | 5 | 761 | 2 |
| de-watered shifted gas | 40 | 23 | 131 | 1892 | 12 | 440 | 5 | 9 | 0 |
| PSA waste gas | 40 | 2 | 131 | 189 | 12 | 440 | 5 | 9 | 0 |
| PSA hydrogen stream | 40 | 23 | 0 | 1703 | 0 | 0 | 0 | 0 | 0 |
| product hydrogen | 40 | 23 | 0 | 1664 | 0 | 0 | 0 | 0 | 0 |

*includes higher hydrocarbons and corresponds to formula CH$_{3.85}$

EXAMPLE 2

In this example the procedure of Example 1 is modified so as to produce a greater amount of methanol, about 103 te/day, and essentially the same amount of hydrogen, about 80 te/day, from essentially the same total amount of natural gas. In order to increase the proportion of methanol produced, a greater proportion of the natural gas feedstock is subjected to reforming and no shift stage is used. Thus the unreacted gas remaining after separation of the methanol in separator 28 is fed directly to the pressure swing adsorption unit 39. In this example, 34% of the de-watered reformed gas is used as the methanol synthesis quench gas. Since there is no shift stage, less hydrogen is produced and the waste gas from the PSA has a greater fuel value since it contains more carbon monoxide. Hence, despite the increased amount of natural gas used for reforming, the amount of natural gas required as fuel is reduced. The temperature pressure, and flow rates (rounded to the nearest integer) of the various streams are shown in the following table.

TABLE 2

| Stream | T (° C.) | P (bar abs.) | CH$_4$ | H$_2$ | CO | CO$_2$ | N$_2$ | H$_2$O | CH$_3$OH |
|---|---|---|---|---|---|---|---|---|---|
| natural gas feed | 40 | 31 | 899* | 0 | 0 | 5 | 7 | 0 | 0 |
| natural gas fuel | 40 | 31 | 95* | 0 | 0 | 1 | 1 | 0 | 0 |
| process feed | 40 | 31 | 804* | 0 | 0 | 5 | 6 | 0 | 0 |
| hydrogen recycle | 40 | 31 | 0 | 39 | 0 | 0 | 0 | 0 | 0 |
| process steam | 340 | 40 | 0 | 0 | 0 | 0 | 0 | 2412 | 0 |
| reformer feed | 540 | 30 | 804* | 39 | 0 | 5 | 6 | 2412 | 0 |
| reformed gas | 865 | 27 | 150 | 2176 | 419 | 239 | 6 | 1524 | 0 |
| de-watered reformed gas | 40 | 27 | 150 | 2175 | 419 | 239 | 6 | 9 | 0 |
| ex-methanol synthesis | 242 | 24 | 150 | 1894 | 290 | 231 | 6 | 17 | 137 |
| wash water | 40 | 40 | 0 | 0 | 0 | 0 | 0 | 50 | 0 |
| crude methanol | 40 | 24 | 0 | 0 | 0 | 1 | 0 | 65 | 135 |
| unreacted gas to PSA | 40 | 24 | 150 | 1894 | 290 | 230 | 6 | 2 | 2 |
| PSA waste gas | 40 | 2 | 150 | 189 | 290 | 230 | 6 | 2 | 2 |
| PSA hydrogen stream | 40 | 24 | 0 | 1705 | 0 | 0 | 0 | 0 | 0 |
| product hydrogen | 40 | 24 | 0 | 1665 | 0 | 0 | 0 | 0 | 0 |

*includes higher hydrocarbons and corresponds to formula CH$_{3.85}$

EXAMPLE 3

In this example, to make an even greater proportion of methanol, about 194 te/day, but less hydrogen, about 62 te/day, the procedure of Example 2 is modified by using a higher reforming pressure and two methanol synthesis stages in series with separation, with water washing, of the methanol after each stage. Each methanol synthesis stage employs 5 beds with injection of 31% of the de-watered reformed gas as quench gas in the first stage and 48% of the unreacted gas from the first stage as quench gas in the second stage. The temperature, pressure, and flow rates (rounded to the nearest integer) of the various streams are shown in the following table.

TABLE 3

| Stream | T (° C.) | P (bar abs.) | CH$_4$ | H$_2$ | CO | CO$_2$ | N$_2$ | H$_2$O | CH$_3$OH |
|---|---|---|---|---|---|---|---|---|---|
| natural gas feed | 40 | 41 | 887* | 0 | 0 | 5 | 7 | 0 | 0 |
| natural gas fuel | 40 | 41 | 83* | 0 | 0 | 0 | 1 | 0 | 0 |
| process feed | 40 | 41 | 804* | 0 | 0 | 5 | 6 | 0 | 0 |
| hydrogen recycle | 40 | 41 | 0 | 39 | 0 | 0 | 0 | 0 | 0 |
| process steam | 340 | 50 | 0 | 0 | 0 | 0 | 0 | 2412 | 0 |
| reformer feed | 540 | 40 | 804* | 39 | 0 | 5 | 6 | 2412 | 0 |
| reformed gas | 865 | 37 | 202 | 2017 | 371 | 236 | 6 | 1579 | 0 |
| de-watered reformed gas | 40 | 37 | 202 | 2017 | 371 | 236 | 6 | 7 | 0 |
| ex-synthesis stage 1 | 242 | 34 | 202 | 1705 | 236 | 221 | 6 | 21 | 149 |
| stage 1 wash water | 40 | 40 | 0 | 0 | 0 | 0 | 0 | 50 | 0 |
| crude methanol ex-stage 1 | 40 | 34 | 0 | 1 | 0 | 2 | 0 | 70 | 148 |
| synthesis stage 2 feed | 40 | 34 | 202 | 1704 | 236 | 219 | 6 | 1 | 1 |
| ex-synthesis stage 2 | 251 | 32 | 202 | 1473 | 154 | 197 | 6 | 23 | 106 |
| stage 2 wash water | 40 | 40 | 0 | 0 | 0 | 0 | 0 | 50 | 0 |
| crude methanol ex-stage 2 | 40 | 31 | 0 | 0 | 0 | 1 | 0 | 72 | 105 |
| unreacted gas to PSA | 40 | 31 | 202 | 1473 | 154 | 196 | 6 | 2 | 1 |
| PSA waste gas | 40 | 2 | 202 | 147 | 154 | 196 | 6 | 2 | 1 |
| PSA hydrogen stream | 40 | 31 | 0 | 1326 | 0 | 0 | 0 | 0 | 0 |
| product hydrogen | 40 | 31 | 0 | 1286 | 0 | 0 | 0 | 0 | 0 |

*includes higher hydrocarbons and corresponds to formula CH$_{3.85}$

What is claimed is:

1. A process for the co-production of hydrogen and methanol comprising:
   (a) subjecting a hydrocarbon feedstock to steam reforming at an elevated pressure and temperature to produce a reformed gas stream containing hydrogen, carbon oxides, methane and unreacted steam;
   (b) cooling the reformed gas to condense steam therein and separating condensed water;
   (c) without further compressing the resultant de-watered reformed gas, subjecting the de-watered reformed gas to once-through methanol synthesis and separating synthesized methanol from the product to leave an unreacted gas stream; and
   (d) separating hydrogen from the unreacted gas stream.

2. A process according to claim 1 wherein the unreacted gas is subjected to the shift reaction with steam prior to separation of hydrogen.

3. A process according to claim 2 wherein steam is added to part of the unreacted gas remaining after separation of synthesised methanol and the mixture subjected to the shift reaction and the remainder of the unreacted gas is used as quench gas to moderate the shift reaction.

4. A process according to claim 1 wherein there are two or more methanol synthesis stages with separation of synthesised methanol between stages.

5. A process according to claim 1 wherein synthesized methanol is separated from the reacted gas by washing with water.

6. A process for the co-production of hydrogen and methanol comprising:
   (a) subjecting a hydrocarbon feedstock to steam reforming at an elevated pressure and temperature to produce a reformed gas stream containing hydrogen, carbon oxides, methane and unreacted steam;
   (b) cooling the reformed gas to condense steam therein and separating condensed water;
   (c) without further comprising the resultant de-watered reformed gas and without addition of steam, subjecting the de-watered reformed gas to a once-through methanol synthesis and separating synthesized methanol from the product to leave an unreacted gas stream; and
   (d) separating hydrogen from the unreacted gas stream without subjecting the unreacted gas stream to a shift reaction.

* * * * *